United States Patent
Venturini et al.

(10) Patent No.: US 6,840,939 B2
(45) Date of Patent: Jan. 11, 2005

(54) AXIAL EXTERNAL FIXATOR

(75) Inventors: Daniele Venturini, Povegliano Veronese (IT); Michele Coati, San Pietro in Cariano (IT); Luigi Rossi, Peschiera del Garda (IT)

(73) Assignee: Orthofix S.r.l. (IT)

( * ) Notice: Subject to any disclaimer, the term of this patent is extended or adjusted under 35 U.S.C. 154(b) by 0 days.

(21) Appl. No.: 10/276,905

(22) PCT Filed: Mar. 1, 2001

(86) PCT No.: PCT/EP01/02312

§ 371 (c)(1),
(2), (4) Date: Nov. 19, 2002

(87) PCT Pub. No.: WO01/91654

PCT Pub. Date: Dec. 6, 2001

(65) Prior Publication Data

US 2003/0125736 A1 Jul. 3, 2003

(30) Foreign Application Priority Data

May 26, 2000 (EP) .......................................... 00830381

(51) Int. Cl.$^7$ ............................................. A61B 17/64
(52) U.S. Cl. ...................................................... 606/54
(58) Field of Search ..................................... 606/53–59

(56) References Cited

U.S. PATENT DOCUMENTS

| | | | | |
|---|---|---|---|---|
| RE31,809 E | * | 1/1985 | Danieletto et al. | 606/57 |
| 5,827,282 A | * | 10/1998 | Pennig | 606/54 |
| 5,951,556 A | * | 9/1999 | Faccioli et al. | 606/65 |
| 6,036,691 A | * | 3/2000 | Richardson | 606/57 |

FOREIGN PATENT DOCUMENTS

| | | |
|---|---|---|
| WO | WO-94/02078 A1 | 2/1994 |
| WO | WO-95/16402 A1 | 6/1995 |
| WO | WO-97/03620 A1 | 2/1997 |

* cited by examiner

Primary Examiner—Kevin Shaver
Assistant Examiner—Michael B. Priddy
(74) Attorney, Agent, or Firm—Akerman Senterfitt

(57) ABSTRACT

The invention relates to a new type of axial unilateral external splint device for stabilizing bone fractures, comprising an extendible rod-like middle body (2) and oppositely located bone screw clamps (5, 6) which are articulated to respective ends (3, 4) of the rod-like middle body (2) by means of ball joints. Advantageously, a ball-and-socket joint (16) is mounted to each clamp (5, 6), within a main body (20) with which a bone screw clamping arrangement (25, 26, 21, 22, 23) is associated or co-operates. Also provided are ancillary members (30) adapted for removable association with the end of each clamp (5, 6) to allow each clamp to be more suitable for use, depending on the different operative installation conditions of the fixator.

11 Claims, 3 Drawing Sheets

AXIAL EXTERNAL FIXATOR

DESCRIPTION

1. Field of the Invention

This invention broadly relates to an improved axial external fixator for stabilizing bone fractures in orthopedic surgery.

More particularly, the invention relates to an axial and unilateral external fixator, comprising an extendible rod-like middle body and oppositely located bone screw clamps which are articulated to the respective ends of the rod-like middle body by means of ball joints.

2. Prior Art

In this specific field, unilateral external fixators have long been employed to foster recovery of bone fractures thereby fixing the bone fragments firmly in place.

Such external fixators comprise a middle body of substantially cylindrical shape which can be axially extendible and which has bone screw clamps articulated to its opposite ends by means of ball joints. The clamps are connected to rod-like fixing bone screws which have been implanted into the cortex of a broken bone on opposite sides of the fracture. Usually, two or three screws are enough to provide a hold.

One example is an external fixator for stabilizing tibia fractures disclosed in the European Patent N. 0 609 409 by the same Applicant.

A variety of splint devices to cope with different typologies of fractures and traumatisms are normally available from their suppliers.

Thus, there are tibia and femurfixators, humerus fixators, joints, such as the ankle and the elbow, fixators, and wrist fixators.

All these fixators are comparable in constitution and include similar components; however, different types of fractures lead to the necessity of producing a plurality of fixators having different sizes and configurations.

However, such a comprehensive stock of different fixators can only reflect in increased manufacturing costs of each typology because of standard mass production methods being impraticable.

Also, the current technological tendency to produce fixators which have portions or parts moulded out of transparent materials to X-radiation makes the supply of many and different types of fixators even less economical.

The underlying technical problem of this invention is to contrive a unilateral external fixator, for stabilizing bone fractures, with structural and functional features such to lower the manufacturing costs of fixators supplied in a range of different types.

SUMMARY OF THE INVENTION

The principle of this invention is one of providing a bone screw clamp which is universally applicable to different configurations of fixators.

Based on this principle, the technical problem is solved by this invention providing a fixator as previously indicated and defined in the characterizing portions of claims 1 and following.

The features and advantages of the external fixator according to the invention will be apparent from the following description of an embodiment thereof, given by way of non-limitative example with reference to the accompanying drawings.

DETAILED DESCRIPTION

Figure 1:
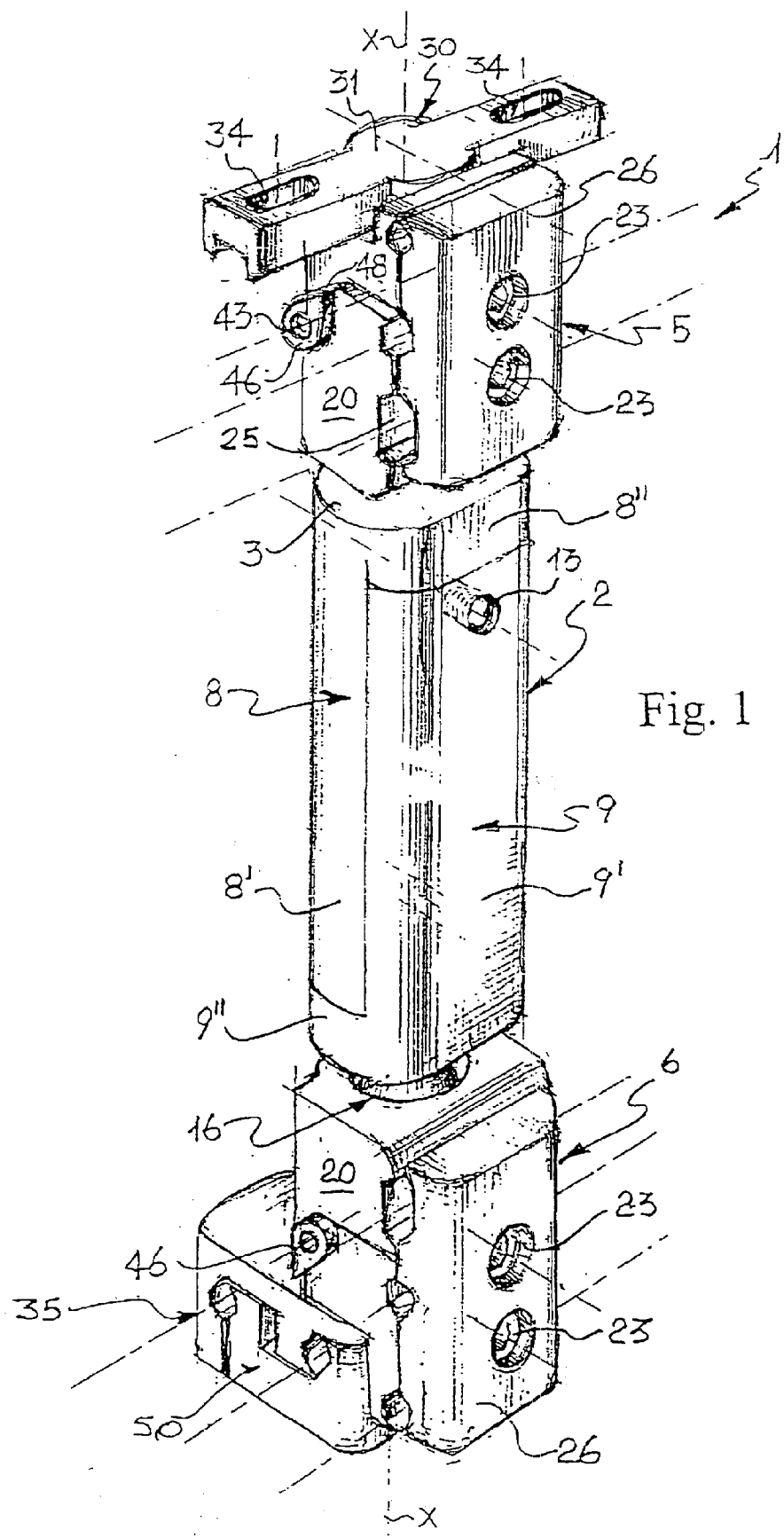
FIG. 1 shows a vertical perspective view of an axial unilateral external fixator embodying this invention.
Figure 2:
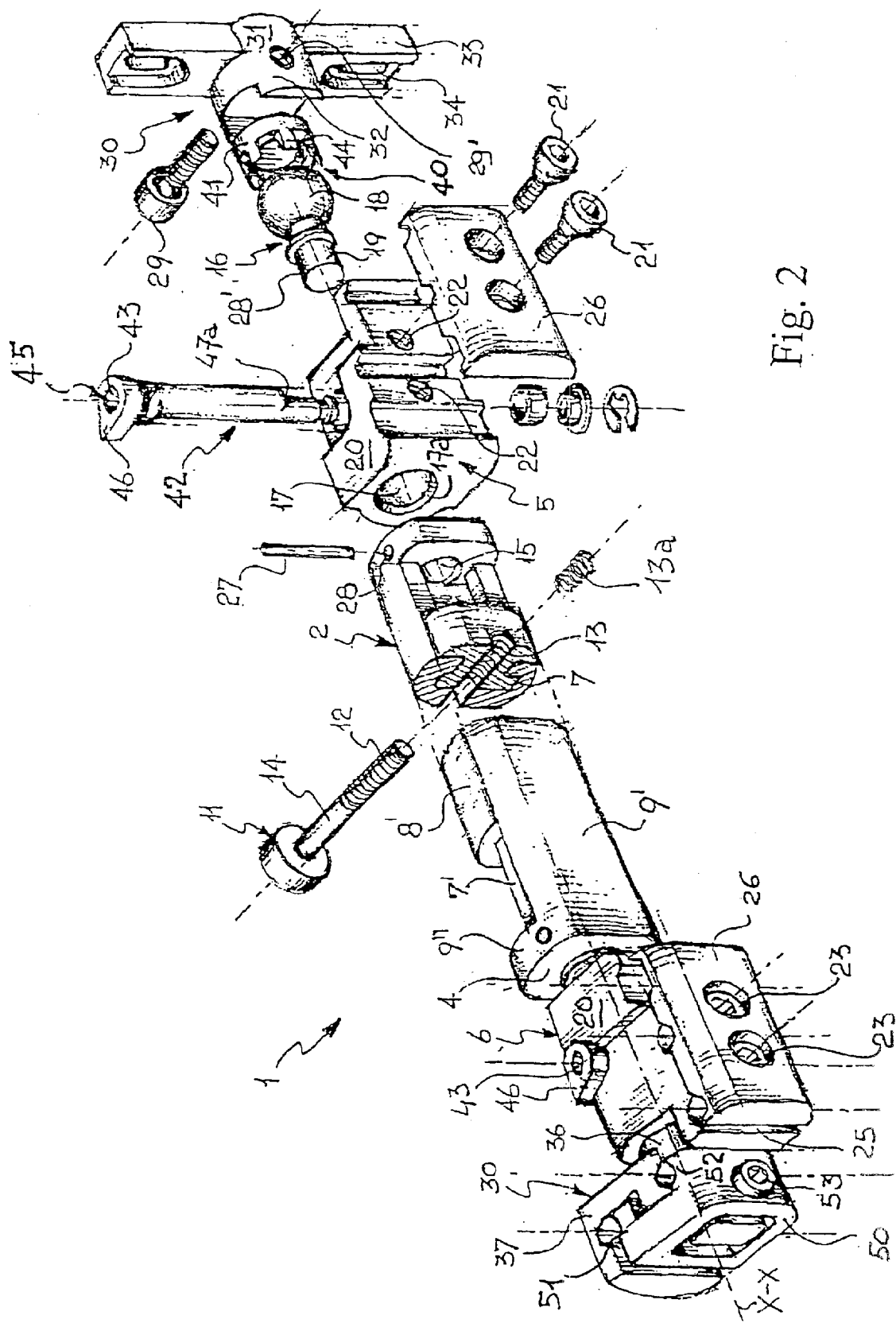
FIG. 2 shows an exploded perspective view of the fixator shown in FIG. 1.

With reference to the drawing views, an axial unilateral external fixator for stabilizing bone fractures in orthopedic surgery formed according to the present invention, is totally shown at 1.

The fixator 1 comprises a rod-like middle body 2 having an axis x-x and opposite ends 3, 4 which are articulated to the respective bone screw clamps 5, 6.

Advantageously, both the rod-like middle body 2 and the clamps 5, 6 are preferably made out of a transparent material to X-radiation, such as a polyetherketone plastics matrix known as "Peek", as reinforced by a predetermined amount of carbon fibers with the aim to obtain a suitable rigidity.

More particularly, the rod-like middle body 2 is axially extendible since it is formed by a first 8 and a second 9 mating part of prismatic shape. The parts 8 and 9 telescopicallyslide on each other.

Each of said parts 8, 9 comprises a first portion 8', 9' of elongate semicylindrical shape which is integrally formed with a second cylindrical end portion 8", 9" of short length. Each part, 8 and 9, is therefore L-shaped if seen sideways.

The semicylindrical sliding portions 8', 9' are joined to each other along a driving groove 7, longitudinally formed in the portion 8', and through a corresponding slide 7' longitudinally formed in the other portion 9'. In particular, the portion 8' essentially has a C-shaped section, while the other portion 9' is formed with a longitudinal rib having a T-shaped section to define said slide 7'.

Of course, other driving/sliding combinations can be provided within the scope of the invention.

Advantageously, a means of stopping said parts 8 and 9 in their sliding movement is provided.

Figure 3:
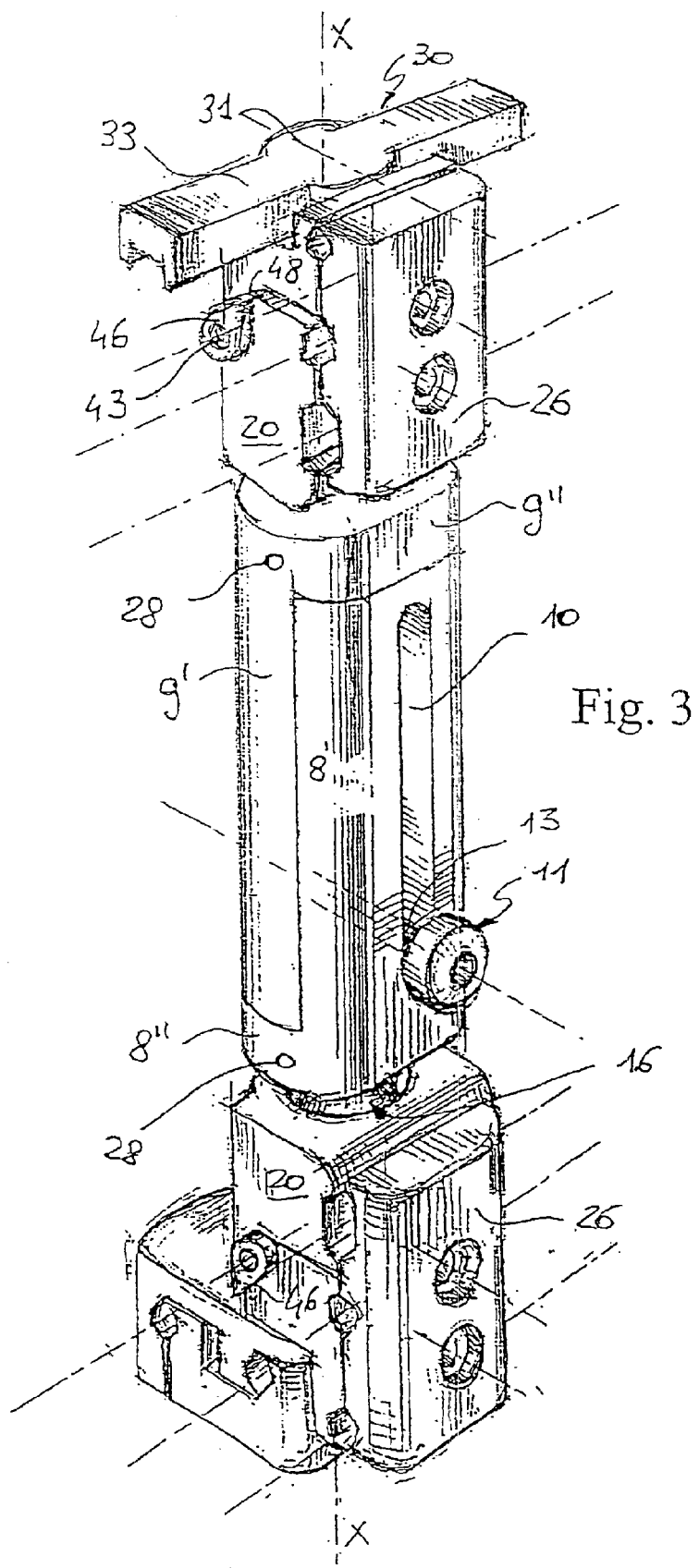
FIG. 3 shows another vertical perspective view of the fixator shown in FIG. 1.

This stop means comprises a locking screw 11, perpendicularly extended to the axis x—x, which locking screw has a threaded end portion 12 engaged in a threaded hole 13 formed in the slideway 7' and reinforced by a "Heli-coil" 13a. A fastener may be provided to hold the threads. In addition, the portion 8' of the part 8 is formed with a clearance slot 10 which longitudinally spans most of the portion 8, as shown in FIG. 3. The screw 11 goes through the slot 10, preferably with a smooth section of its shank 14, to ease the sliding movement and the amplitude of the portions 8 and 9 on each other.

The screw 11 is an Allen screw for convenient operation with a wrench.

By loosening and tightening the screw 11, the extension of the rod-like middle body 2 of the fixator 1 can be adjusted, depending on the different dimensions of a broken bone. To the contrary, any rotations of the parts 8 and 9 about the axis of the rod-like middle body 2 occur, because of the C- and T-shaped sections of the driving groove and of the slide.

In the compact setting of the rod-like middle body 2, the portions 8' and 9' of the parts 8 and 9 are fully superposed, with one abutting the cylindrical end portion 9", 8" of the other.

As mentioned above, the opposite ends 3, 4 of the rod-like middle body 2 are articulated to the respective clamps 5, 6 of the bone screws by means of ball joints.

Each joint comprises a ball-and-socket joint 16 mounted to each clamp 5,6.

In particular the ball-and-socket joint 16 includes a cylindrical socket 17 delimited by a ball-retaining rim 17a and provided in each clamp 5, 6, and has a ball head 18 lodged in the socket 17. The ball head 18 has a shank 19 adapted to be received in a corresponding socket 15 in each of the ends 3, 4 of the rod-like middle body 2.

The socket 15 lodging the shank 19 is formed in a quite central position in the end portions 8" and 9" of the parts 8 and 9. Briefly, the socket 15 is coaxial to the axis x—x, and the shank 19 is held in the socket 15 by a removable retention means such as a lockpin 27 passing through a hole 28 transversal to the axis x—x passing through the portion 8" and a corresponding hole 28' transversal to the shank 19. This hole is intended to lodge the lockpin 27 of the shank 19, as well as to index the attachment of a dynamizing compressor as described in the European Patent 0 734 233, for example.

Each of the clamps 5 and 6 comprises a main body 20, substantially prismatic in shape, wherein the cylindrical socket 17, which lodges the ball head 18, is formed.

A flange 26 is removably associated with the main body 20 for closing the clamp onto bone screws, in the example two screws 21 lying in a parallel plane to the plane led through the axis x—x, and being placed a predetermined distance away therefrom.

More particularly, the main body 20 has a side wall 25 of shaped contour. The contour of the flange 26 substantially mates with the side wall 25, such that the side wall 25 and the flange 26 will joint like the jaws of a vise, so locking the bone screws.

Preferably, the removable coupling of the body 20 and the flange 26 occurs by the engagement of a pair of screws 21 in corresponding threaded sockets 22 provided in the main body 20, along with optional strengthening bushes, through clearance holes 23 passing in the flange 26. The threaded sockets 22 are formed on the side wall 25 of the body 20.

This particular configuration enables the bone screws to be held in the clamp substantially alongside the ball-and-socket joint, thereby achieving a highly compact structure of the overall clamp.

Advantageously, a means 40 of locking the ball-and-socket joint 16 in a selected angular position is also provided. This locking means 40 comprises a slider 41 which is guided for movement inside the cylindrical socket 17 of the main body 20 in the direction toward the ball head 18, by the action of a driving means 42.

This driving means 42 comprises a shaft 47 which transversely extends to the socket 17 and is provided with a cam 47a acting on the slider 41. The shaft 47 can be manually rotated with a suitable wrench, and is purposely formed with a recessed hexagon 43 at an accessible end thereof.

Specifically, the slider 41 comprises a cylindrical rim having a plurality of contrate teeth 44, all extending towards the same direction parallel to the axis of the rim. These teeth 44 are intended to bite into the surface of the ball head 18, upon actuation of the driving means 42, and form a respective plurality of impressions of a suitable depth therein, e.g. a few tenths of a millimeter deep. In this way, the ball head 18, and hence the ball-and-socket joint 16, is practically locked in a positive manner.

A stroke limiting means 45 of the slider 41 is provided in order to have the teeth 44 bite a predetermined depth into the ball head 18. This limiting means 45 comprises a radial nose 46 integral with the shaft 47, which is set flush with the exterior of the main body 20 and arranged to abut against a stop 48 formed on the main body 20, at an appropriate angular setting of the shaft 47 relative to the main body 20.

With the radial nose 46 abutting the stop 48, the plurality of teeth 44 of the slider 41 will have sunk a maximum anticipated depth into the surface of the ball head.

In assembling one of the clamps, 5 or 6, first the ball head 18 of the joint 16 is inserted into the cylindrical socket 17 with the shank 19 abutting out of the main body 20. Then the slider 41 with its teeth 44 facing the ball head 18, and the shaft 47 to stop the previous parts from coming off, is assembled. The shaft 47 is positioned such that an end portion of the cylindrical socket 17 is left available for receiving an additional cylindrical member as described herein below.

The cylindrical socket 17 at the free end of the main body 20 is also used for holding an ancillary member 30 which effectively makes the clamp, 5 or 6, more versatile, depending on the different installations of the fixator.

For example, an ancillary member 30 is illustrated by a T-connection member 31, for connecting the clamp 5 to a ring of a ring fixator known in the art as the Ilizarov system.

The connecting member 31 comprises a cylindrical shank 32 pivotally fitting in the same cylindrical socket 17 that accommodates the ball head 18 of the ball-and-socket joint 16.

A locking screw 29 engages in a threaded hole 29' that can be equipped with a fastener. Such hole is transversely formed at the shank 32 and through a slotted hole provided in the main body 20 close to the end thereof opposite to the ball joint 16. The connecting member 31 further comprises a plate-like portion 33 which is formed integral with the shank 32 and extends perpendicularly to it. This portion 33 has oppositely located wings which are penetrated by slotted holes 34 for connection to a ring of an external splint in the Ilizarov system.

In this way, a clamp 5 or 6 provided with the connecting member 31 can be fastened to a ring in the Ilizarov system to produce a so-called "hybrid splint", that is an external fixator, comprising an axial fixator and at least one ring, which combines the advantageous features of the fixators and unilateral axial fixators.

Another ancillary member 30 is illustrated in the drawings by a metaphysis clamp 35 for clamping to bone screws which lie in a substantially perpendicular plane to the axis x—x and, therefore, transversal to the lying plane containing said bone screws held between the walls 25 and 26 of the clamp 5 or 6.

More particularly, a metaphysis clamp 35 allows to secure the fixator to bone screws implanted in the proximal or the distal end portions of a tibia, or implanted in the distal end portion of a femur.

The metaphysis clamp 35 is held in one of the clamps 5 or 6, in the same way as the connecting member 31. In fact, the metaphysis clamp 35 would include, same as the connecting member 31, a cylindrical shank 36 which fits in the cylindrical socket 17, and one end 37 integrally formed with the shank 36 and perpendicularly extending to the latter.

The end 37 is configured with a U-shaped portion which is integrally formed integrally with the shank 36, offset therefrom. The U-shaped portion basically comprises a pair of walls 38; 39 extending parallel to and spaced from each other. A semi-cylindrical groove 38', 39' is provided at the bottom of each wall 38, 39 on the same side, which groove defines half of a socket to accommodate a corresponding metaphysis bone screw, that is a screw implanted in the proximal or the distal end of a tibia, or the distal end of a femur, in a substantially perpendicular plane to the plane of the axis x—x.

Advantageously, the portion 37 includes a means of clamping metaphysis bone screws. This clamping means comprises a slider 50 which is mounted on the portion 37 for sliding movement along a concurrent direction to the direction in which the flange 26 is clamped against the wall 25.

Such slider 50 has a rectangular base 49 formed with a window 49a, and has two plate-like lugs 51, 52 which are integrally formed with the base 49 at the short sides thereof.

The plate-like lugs 51, 52 cooperate with the walls 38 and 39 to clamp the metaphysis screws therebetween. More particularly, the slider 50 is sliding mounted on a narrowing down end of the wall 39 through the window 49a, such that the lug 51 will be facing the portion 37 and movable between the walls 38 and 39 parallel thereto.

Provided on the same side in the free ends of the lugs 51 and 52 are provided respective semi cylindrical grooves 51', 52', each defining half of a socket accommodating a corresponding metaphysis bone screw. With the slider 50 assembled to the portion 37, the grooves 38' and 51' face each other, and so do the grooves 39' and 52', ready for clamping onto a corresponding metaphysis screw.

A locking screw 53 passes through a hole laterally provided in the slider 50 and engages in a threaded bush which is accommodated in a hole formed close to the free end of the wall 39 to lock the slider 50 in place, clamping onto the metaphysis screws.

In this way, i.e. with the screws, including the side ones between the wall 25 and the flange 26 and the metaphysis ones between the slider 50 and the portion 37, all brought to a tightened state by displacements occurring all in the same direction, their mutual positions are retained even when their diameters change, for example, from screws with a diameter of 6 mm to screws with a diameter of 8 mm throughout.

The splint device of this invention does solve the technical problem and offers a number of advantages, foremost among which is that the clamps are of universal utility, unlike prior solutions.

In fact, the middle body 2 can have opposite clamps associated with it, which serve different functions but stem all from a common basic structure.

Furthermore, the fixator made of a transparent material to X-radiation allows the orthopedic surgeon to radiograph the affected region without suffering interference from bulky objects.

Also, it should be noted that the middle body accounts for a major portion of the overall length of the fixator according to the invention, and allows the fixator length to be adjusted for almost any traumatic situations.

It should be further noted that the multiple impressions produced by the contrate teeth in the surface of the ball head, so that in practice the ball-and-socket joint can be set positively in any desired angular position, also forbid the re-use of the clamps, which are therefore disposable clamps. This represents an added advantage from both the sanitary and the safety standpoints.

What is claimed is:

1. An axial unilateral external fixator for stabilizing bone fractures, comprising;

an extoadibic rod-like middle body;

oppositely located bone screw clamps which are articulated to respective ends of the rod-like middle body by means of ball joints; and an ancillary member removably associated with a free end of a clamp to allow the connection to another fixator or bone fixing screws wherein each of said bone screw clamps comprises a main body with which a clamping arrangement for bone screws is associated, wherein a ball-and-socket joint is mounted to each clamp, within a said main body; and wherein the ball-and-socket joint comprises a cylindrical socket formed in the main body of each bone screw clamp, and a ball head lodged in the cylindrical socket and having a shank removably inserted in a corresponding socket at the end of the rod-like middle body.

2. An external fixator according to claim 1, wherein said bone screw clamping arrangement comprises a shaped side wall of said main body and a flange having a contour mating said side wall and removably made fast therewith as the bone screws are tightened.

3. An external fixator according to claim 2, wherein said rod-like middle body is formed of a transparent material to X-radiation.

4. An external fixator according to claim 1 wherein said rod-like middle body comprises two prismatic parts telescopically sliding on each other.

5. An external fixator according to claim 4, further comprising a locking arrangement to stop said parts from sliding.

6. An external fixator according to claim 1, wherein said clamps are formed out of a transparent material to X-radiation.

7. An external fixator according to claim 1, wherein said rod-like middle body has a longitudinal axis, and wherein said boric screw clamping arrangement secures the scrawl to the clamp along a plane lying substantially parallel to and spaced apart from the plane that contains said axis.

8. An external fixator according to claim 1, wherein said ancillary member is pivotally mounted in said cylindrical socket at the free end of said main body.

9. An external fixator, according to claim 8, wherein ancillary member comprises a cylindrical shank inserted into said cylindrical socket and a portion transverse to the shank integrally formed with the latter.

10. An external fixator according to claim 1, wherein said ancillary member comprises a cylindrical shank inserted into said cylindrical socket and a metaphysis clamp connected to said shank.

11. An external fixator according to claim 10, wherein said metaphysis clamp comprises a metaphysis screw clamping arrangement whose moving parts are movable to the same direction as the moving parts of the bone screw clamping arrangement.

* * * * *

UNITED STATES PATENT AND TRADEMARK OFFICE
CERTIFICATE OF CORRECTION

PATENT NO.        : 6,840,939 B2
APPLICATION NO.   : 10/276905
DATED             : January 11, 2005
INVENTOR(S)       : Venturini et al.

It is certified that error appears in the above-identified patent and that said Letters Patent is hereby corrected as shown below:

Column 1, line 27, insert a space between "femur" and "fixators"

Column 2, lines 27 & 28, replace "telescopi-callyslide" with --telescopically side--

Column 4, line 66, replace "integrally formed integrally with the shank" with --formed integrally with the shank--

Column 6, line 6, replace "extoadibic" with --extendible--

Column 6, line 19, delete "a" before "said main body"

Column 6, line 31, insert --out-- after "formed"

Column 6, line 43, replace "boric" with --bone--

Column 6, line 43, replace "scrawl" with --screws--

Signed and Sealed this

Twenty-third Day of January, 2007

JON W. DUDAS
*Director of the United States Patent and Trademark Office*